US00PP19552P3

(12) United States Plant Patent
Lowry

(10) Patent No.: US PP19,552 P3
(45) Date of Patent: Dec. 9, 2008

(54) PEAR TREE NAMED 'LOWRY RED'

(50) Latin Name: *Pyrus communis L*
Varietal Denomination: Lowry Red

(75) Inventor: David Lowry, Phoenix, OR (US)

(73) Assignee: Associated Fruit Company, Phoenix, OR (US)

( * ) Notice: Subject to any disclaimer, the term of this patent is extended or adjusted under 35 U.S.C. 154(b) by 165 days.

(21) Appl. No.: 11/386,183

(22) Filed: Mar. 21, 2006

(65) Prior Publication Data

US 2007/0226856 P1 Sep. 27, 2007

(51) Int. Cl.
*A01H 5/00* (2006.01)

(52) U.S. Cl. ..... Plt./176

(58) Field of Classification Search ..... Plt./176
See application file for complete search history.

*Primary Examiner*—Kent L Bell
(74) *Attorney, Agent, or Firm*—Wells St. John P.S.

(57) ABSTRACT

A new and distinct variety of pear tree 'Pyrus communis L' and which is denominated varietally as 'LOWRY RED' and which produces an attractively colored red pear which is mature for harvesting and shipment approximately after September 18 under the ecological conditions prevailing near Phoenix, Oreg.

1 Drawing Sheet

BACKGROUND OF THE NEW VARIETY

The present invention relates to a new, novel and distinct variety of pear tree 'Pyrus communis L' and which has been denominated varietally as "'LOWRY RED'."

The present variety of pear tree resulted from a hybrid cross which was performed by the inventor David B. Lowry in April 1985 of a 'Forelle' pear tree (unpatented) with that of a red 'Bartlett' pear tree (also unpatented). The controlled hybrid cross which was conducted in 1985 produced an original seedling which first produced fruit that was evaluated during the 1997 growing season. The new variety displayed promising characteristics and was then selected for advanced evaluation and reproduction.

Asexual reproduction of this new and distinct variety of pear tree was accomplished by grafting the new variety into 10 test trees during February, 2000. These test trees were originally grafted onto unnamed pear seedling rootstock at an orchard near Phoenix, Oreg. The grafted trees produced a few fruit in September, 2002, and subsequently produced normal crop loads in years 2003 and 2004, respectively. Subsequent evaluations of the characteristics of these asexual reproduced trees run true to the original tree. In this regard, all characteristics of the original seedling, and its fruit, were established and transmitted through the succeeding asexual propagations.

The 'Lowry Red' is a new and distinct variety of pear tree which produces fruit having a large size and which is highly colored, and which further matures during middle to late September. The fruit produced by this pear tree which is grown near Phoenix, Oreg. has a good flavor, and a high degree of uniformity throughout the tree. In relative comparison to the parents, the fruit of the 'Lowry Red' is mature for harvesting and shipment about one month later than the common commercial 'Bartlett' pear varieties, and its red spots such as 'Red Bartlett' (all unpatented); and about one week earlier than the pear tree variety 'Forelle' (also unpatented) when grown under similar conditions and at the same geographical location. In relative comparison to the 'Bartlett' pear tree, the new variety produces fruit which are equal to or larger than the fruit of the 'Bartlett' pear tree (unpatented) when grown under the ecological conditions prevailing near Phoenix, Oreg. Further, the fruit of the present variety is substantially larger than the fruit produced by the 'Forelle' pear tree. Additionally, the near variety has a red skin color which is more intense than that produced by the 'Red Bartlett' pear tree or the 'Forelle' pear tree. Still further, the present variety produces fruit having a uniform size and shape which is generally considered more uniform than that of either parent.

BRIEF DESCRIPTION OF THE DRAWING

The accompanying drawing which is provided is a color photograph of the new present variety of pear tree. The present photograph depicts three mature fruit, each of which has been dissected substantially along the longitudinal plane, and which reveals the flesh and the skin characteristics thereof. The external coloration of the fruit as shown in the photograph is sufficiently matured for harvesting and shipment. Additionally, the photograph displays a sample vegetative shoot bearing typical leaves and several seeds. The colors in this photograph are as nearly true as is reasonably possible on a color representation of this type. Due to chemical development, processing and printing, the leaves and fruit depicted in these photographs may or may not be accurate when compared to the actual specimen. For this reason, future color reference should be made to the color plates as provided by The Royal Horticultural Society of Great Britain, and the descriptions as provided for hereinafter.

DETAILED DESCRIPTION

Referring more specifically to the pomological details of this new and distinct variety of pear tree, the following has been observed on trees that were six years old during the 2005 growing season at orchards which are located near Phoenix, Oreg. All major color code designations are by reference to the R.H.S. Colour Chart, 3rd Edition provided by The Royal Horticultural Society of Great Britain. Common color names are used occasionally.

TREE

*Vigor.*—Average in relative comparison to the 'Bartlett' pear tree (unpatented). The present variety is not as vigorous as the 'Bartlett' pear tree. The new variety is hardy when grown under the climatic conditions prevailing in the Medford, Oreg. pear growing district of sourthern Oregon.

*Form.*—Generally — Considered upright to upright-spreading.

Trees of the present variety range in size from about 4.6 meters to about 5.3 meters in height and from about 1.5 meters to about 1.7 meters in width.

*Current season growth.*—Length — In vigorous areas of the tree, this can range from about 30.5 cm. to as much as 121.9 cm.

*Orchard spacing.*—Currently, the trees of the present variety are spaced at distances of about 1.2 meters in rows. The rows are positioned approximately 17 feet apart.

The present tree has been pruned annually into a central leader system where a single trunk is maintained in an upright, vertical position with smaller spaced secondary limbs arise from around the central leader.

Regularity of bearing. —The present variety is a regular and productive bearer of attractively colored fruit.

TRUNK

*Diameter.*—Approximately 10 cm. to about 11.5 cm. when measured at the point of grafting which is approximately 30 cm. above ground level.

*Bark surface.*—Generally — Quite variable, being slightly furrowed with both smooth, netted and roughly striated areas.

*Surface color.*—Smooth surfaces have a light grey color (Fan 4, sheet 201-D). Roughened surfaces have a dark grey color (Fan 4, sheet 201-A).

*Bark lenticels.*—Numbers — Numerous.

*Bark lenticels.*—Form — Considered flattened and oval and further having a roughened or corky appearing surface.

*Bark lenticels.*—Size — Variable from about 1 mm. to as large as 9 mm. in width.

*Bark lenticels.*—Height — About 1 mm. to about 2 mm.

*Bark lenticel.*—Color — Considered variable. Calloused bark lenticel surfaces have a brown color (Fan 4, sheet 174-B). Bark lenticels without much callousing have a dark grey color (Fan 4, sheet 201-A).

BRANCHES

*Size.*—Generally considered normal in size and diameter for the species.

*Spreading branches.*—Size — These branches which arise from the central tree axis have a size of about 3 cm. to about 8 cm. in diameter at their base. Smaller spreading branches range from about 1.3 mm. to about 2 mm. in diameter at their bases.

*Spreading branches.*—Surface texture — Typically considered moderately smooth but with some slight netting.

*Branch surface color.*—Typically grey, (Fan 4, Sheet 201-D).

*Branch lenticels.*—Numbers — Numerous and having a flattened oval form.

*Branch lenticels.*—Size — About 1 mm. to about 5 mm. in width.

*Branch lenticels.*—Height — About 1 mm. to about 1.5 mm.

*Lateral branches.*—Size — Smaller lateral branches are often present and arise from the larger spreader branches. These lateral branches can range in size from about 0.7 cm. to about 1.1 cm. in diameter when measured at their base.

2 *year old and older lateral shoot surface.*—Generally speaking, they are considered relatively smooth and glabrous. Although a slight amount of netting can also be present.

*Internodes.*—Length — These shoots can range from about 11 mm. to about 31 mm. between the nodes.

*Lateral branches.*—Color — Typically grey (Fan 4, sheet 201-C).

*Spurs.*—Length — Those spurs occurring on older wood have a length of about 10 mm. to as much as 50 mm. in length, and from about 3 mm. to about 6 mm. in thickness at their bases.

*Spurs.*—Internode length — Variable from about 4 mm. to about 10 mm. between nodes.

*Spur color.*—Grey, (Fan 4, sheet 201-C).

*Mature current season shoots.*—Surface Texture — Smooth and essentially glabrous. Occasionally, a small amount of fine, scattered pubescence can also be present.

*Mature current season shoots.*—Color — Brown (Fan 4, sheet 177-A).

*Mature current season internode lengths.*—Variable from about 20 mm. to about 36 mm.

*Mature current season shoots.*—Lenticels — Considered numerous, prominent and slightly raised with some surface callousing present.

*Mature current season shoots.*—Lenticel Color — Brown (Fan 4, sheet 166-D).

*Immature current season shoots.*—Surface Texture — Relatively smooth, but with fine scattered pubescence occasionally present.

*Immature current season shoots.*—Color — Purple-Brown (Fan 4, sheet 183-A).

*Immature current season shoots.*—Internode Length — About 20 mm. to about 36 mm.

*Immature current season shoots.*—Lenticels — Generally speaking, numerous small, globose to oval lenticels are present. These lenticels range in size from about 0.5 mm. to about 1 mm. in diameter.

*Immature current season shoots.*—Lenticel color — Brown (Fan 4, sheet 165-C).

LEAVES

*Size.*—Considered average for the species. Measurements of the present leaves have been taken from those leaves which have been growing at mid-shoot on the more vigorous, upright, current season shoots.

*Leaf length.*—About 9.7 cm. to about 12.7 cm. including the petiole.

*Leaf width.*—About 4.4 cm. to about 6.3 cm.

*Leaf thickness.*—Considered average for the species.

*Surface texture.*—Both the upper and lower leaf surfaces of the present variety are considered glabrous.

*Mid vein.*—Upper leaf surface texture — Considered glabrous.

*Mid vein.*—Lower leaf surface texture — A small amount of pubescence can be present at the margin of the lower leaf mid-vein where it attaches to the leaf blade.

*Leaf glands.*—No leaf glands are present.

*Leaf form.*—Generally — considered ovate.

*Leaf apex.*—Shape — Acute.

*Leaf base.*—Shape — Rounded. The leaves are usually substantially folded upward from the region of the mid-rib.

*Leaf color.*—Upper Surface — Green (Fan 3, sheet 137-C), and moderately glossy.

*Color.*—Upper vein surface — Yellow-Green (Fan 3, sheet 145-B).

*Color.*—Lower leaf surface — Light green (Fan 3, sheet 138-C), and dull.

*Color.*—Lower vein surface — Yellow-Green (Fan 3, sheet 145-B).

*Leaf margins.*—Form — Variable, but most frequently considered serrate. The serrations are fine. The leaf margins are occasionally slightly undulate.

*Leaf petioles.*—Size — Considered normal for the species.

*Petioles.*—Length — About 29 mm. to about 42 mm.

*Petioles.*—Thickness — About 1.0 mm. to about 1.5 mm. when measured at mid-petiole. The respective petioles widen somewhat at the petiolar base.

*Petioles.*—Color — Yellow-Green (Fan 3, sheet 145-B). A greenish color may appear on ridges subtending the petiole groove (Fan 3, sheet 144-C).

*Petioles.*—Surface Texture — Substantially glabrous, although a small amount of pubescence can sometimes be found near the juncture of the petiole with the lower leaf margin, and along the ridges of the petiole groove.

*Leaf stipules.*—Present, although they may occasionally be absent, and these occur at low frequently late in the growing season.

*Stipules.*—Position — When present, they arise from the petiole at or near the petiole base.

*Leaf stipules.*—Length — About 9 mm. to about 16 mm.

*Leaf stipules.*—Width — About 1 mm. to about 2 mm. in width.

*Leaf stipules.*—Form — Considered linear lanceolate and often cupped or rolled inward.

*Leaf stipules.*—Color — Variable, but most frequently it is a light green (Fan 3, sheet 138-C).

*Leaf stipules.*—Marginal form — Serrate with widely spaced serrations.

FLOWERS

*Bloom timing.*—Date of first bloom for the 'Lowry Red' pear was April 18 in 2006. Full bloom occurred on Apr. 25, 2006. Full bloom for the 'Lowry Red' pear occurred from 5 to 6 days later than the standard commercial 'Bartlett' pear variety at the same location. This date of bloom would be considered mid to late season for the species.

*Flower size.*—The flower size is average for the species. Open flower diameter ranges from 26 mm. to 34 mm. at full expansion. The floral petals can be slightly cupped inwards at full maturity.

*Bloom quantity.*—Bloom quantity is abundant. The amount of bloom produced on the 'Lowry Red' variety is less than the quantity produced on the 'Bartlett' pear. The number of flowers produced from each floral bud ranges from 6 to 10.

*Flower petals.*—Flower petals number 5 on each flower and are of medium size. Petals range from 13 mm. to 15 mm. in length and from 11 mm. to 13 mm. in width. Petal form is somewhat variable, most frequently ovate, but with both obovate and oval forms at times present. The petals can often be cupped inwards. Petal color is white basally and over the center area of the petal (Fan 4, Sheet 155-C). Pink coloration usually is present along the border of the petal apex and down the apical shoulders for a distance of 2 mm. to 3 mm. Color of the darkest border areas is a medium pink (Fan 2, Sheet 62-B). Other areas are a lighter pink (Fan 2, Sheet 62-C). The petal claw is short and truncate in form, ranging from 1.5 mm. to 2.0 mm. in width at the base. Petal margins are variable, from smooth to moderately undulate. The petal apices are also variable, from smoothly rounded to undulate or ruffled.

*Flower pedicel.*—Pedicel size varies from 13 mm. to 17 mm. in length and from 1.0 mm. to 2.0 mm. in diameter at mid-pedicel. Color of the pedicel is generally green (Fan 3, Sheet 138-C) but, at times, with some reddish coloration overlying the green (Fan 4, Sheet 182-C). The pedicel surface is moderately pubescent.

*Floral nectaries.*—Nectary color is a greenish-yellow (Fan 3, Sheet 152-B).

*Flower calyx.*—The surface of the calyx is pubescent, dense at times, with long somewhat matted hairs. Calyx color is greenish (Fan 3, Sheet 138-B) but with some areas overlain with red (Fan 4, Sheet 182-B).

*Flower sepals.*—Sepal size varies from 5 mm. to 7 mm. in length and from 2 mm. to 3 mm. in width at the sepal base. The sepals are somewhat variable in form from linear lanceolate to lanceolate with a wide base. The exterior (lower) surface of the sepal is sparely pubescent and light green in color (Fan 3, Sheet 144-D) with, at times, some pink coloration present, especially at or near the sepal apex (Fan 2, Sheet 58-D).The interior (upper) sepal surface is highly pubescent with dense, light brown colored pubescence (Fan 4, Sheet 164-B). The interior surface color is greenish (Fan 3, Sheet 145-B).

*Anthers and pollen.*—Anther size is average. The anthers range from 1.0 mm. to 1.5 mm. in length and average 1.0 mm. in diameter. Anther color is a dark purple (Fan 2, Sheet 59-A) both ventrally and dorsally. The quantity of pollen is abundant. Pollen color is yellow (Fan 1, Sheet 8-C).

*Stamens.*—Stamen length varies from 5 mm. to 9 mm. The length of the stamens can be about equal or just slightly longer than the height of the pistil at full extension. Color of the filaments is white (Fan 4, Sheet 155-B).

*Pistil.*—The pistil has five styles. Pistil length ranges from 7 mm. 9 mm. The pistil surface is glabrous. Color of the pistil is a pale green (Fan 3, Sheet 145-C).

*Pollination.*—The pollination requirements of the 'Lowry Red' pear are currently unknown, since no controlled pollination studies have been performed. The original test planting of the new pear at Phoenix, Oreg. is adjacent to a commercial planting of the 'Bosc' pear variety (unpatented). At that location, the 'Lowry Red' sets commercially acceptable crops of fruit. The present of the seed in the 'Lowry Red' pears at this location would seem to indicate that the 'Bosc' pear variety would be a suitable pollinator for the new variety.

FRUIT

*Maturity when described.*—The present variety is described at full commercial maturity, and in a firm, ripe condition.

*Date of harvesting.*—18 September through 30 September under the ecological conditions prevailing in Phoenix, Oreg. The fruit of the present variety holds well on the tree, and could occasionally be harvested through the first week of October, if necessary.

*Fruit size.*—Considered large for the variety.

*Transverse diameter.*—Approximately 70 mm. to about 91 mm.

*Axial diameter.*—About 91 mm. to about 115 mm.

*Fruit form.*—Pyriform in its lateral aspect. In its cross-sectional aspect, the fruit is somewhat variable, and most frequently globose with a moderate amount of compression. The fruit is very uniform in appearance on the tree.

*Fruit stem.*—As a general matter, the stem varies from average to slightly slender.

*Fruit stem.*—Length — About 20 mm. to about 27 mm.

*Fruit stem.*—Thickness — About 2.5 mm. to about 3.5 mm. when measured at mid-stem. The stem is slightly thicker at both the basal and distal ends and is often slightly curved.

*Fruit stem.*—Attachment — Variable from vertical to oblique relative to the fruit axis.

*Fruit stem.*—Color — Brown (Fan 4, sheet 177-C); and occasionally an area of green may be present (Fan 3, sheet 153-B).

*Fruit stem.*—Surface — Glabrous, although occasionally a few scattered hairs can be present.

*Stem cavity.*—Form — Irregular and ranging roughly from oval to roughly globose.

*Stem cavity.*—Width — About 11 mm. to about 18 mm.

*Stem cavity.*—Depth — About 4 mm. to about 7 mm. The stem cavity also displays some knobbing and ridging. The stem cavity shoulders are usually rounded.

*Fruit basin.*—Form — Frequently globose, although occasionally it may be somewhat irregular.

*Fruit basin.*—Diameter — About 20 mm. to about 25 mm.

*Fruit basin.*—Depth — About 4 mm. to about 7 mm.

*Fruit basin.*—Shape — The basin shoulders are broad and rounded, and the basin sides are variable from relatively smooth to moderately undulate.

*Calyx lobes.*—Generally — Persistent and can be either upright or reflexed in appearance. The calyx lobes are most frequently separated at the base.

*Calyx opening.*—Form — Usually open, but at times can be partially closed.

*Calyx tubes.*—shape — Funnel-shaped and medium in length with the remnants of the flower styles present within. Remnants of the flower stamen are normally always present and are typically located in a marginal position.

*Core lines.*—Generally — Present, distinct and meeting at the calyx opening.

*Fruit core.*—Position — Distant relative to the stem end of the fruit.

*Fruit carpels.*—Numbers — 5.

*Fruit carpels.*—Form — Frequently closed, although at times slightly opened carpels can be present. Fruit Carpels Color — not observed due to rapid oxidation and color change of the area when the fruit is out.

*Fruit carpels.*—Surface texture — Inner walls of the carpels are smooth.

*Seeds.*—Numbers — Variable from 0 to 7. With full pollination, the fruit of the present variety has the potential of producing 10 seeds. Fruit which have not seeds appear to have been set by parthenocarpy.

*Seeds.*—Shape — Plump, ovate in form and having an acute tip. Although, in some carpels, only a shriveled seed coat may be present.

*Seeds.*—Shape — Ovate in form, with an acute tip.

*Seeds.*—Length — About 9 mm. to about 10 mm.

*Seeds.*—Width — About 5 mm. to about 6 mm.

*Seeds.*—Thickness — Variable from about 3.5 mm. to 4 mm.

*Seeds.*—Color — At harvest time the seeds are light brown (Fan 4, sheet 165-D).

*Seeds.*—Color — After the fruit has softened, the seeds are a darker brown color (Fan 4, sheet 165-B).

*Fruit skin.*—Thickness — Average for the species. This characteristic does not distinguish the present variety.

*Fruit skin.*—Surface texture — Glabrous.

*Fruit skin adherence.*—The skin adheres to the fruit flesh even at full, soft, ripe maturity.

*Fruit (skin) flavor.*—Neutral at full commercial maturity.

*Fruit skin color.*—The present variety has a red blush involving from about 85% to about 100% of the fruit surface.

*Bloom.*—A medium waxy bloom is present, and typically covers the entire fruit surface.

*Fruit blush color.*—Without removal of the blush, the fruit has a slightly dull purple-red color with some overtones of grey (Fan 4, sheet 182-A).

*Fruit blush color.*—With the bloom removed, the fruit has a bright and glossy purple-red color (Fan 4, sheet 185-A).

*Fruit blush color.*—After the fruit has ripened, the fruit takes on a more bright red color. This bright red color in the darker areas is seen at (Fan 1, sheet 42-A), and in the lighter areas has a color of (Fan 1, 42-B).

*Ground color.*—Present and ranging from 0% to about 15% of the fruit surface. At full commercial maturity, the ground color is yellow-green (Fan 3, sheet 150-A).

*Ground color.*—After ripening — the fruit changes to a yellow-gold color (Fan 1, sheet 11-B). Occasionally, a brown russet color can also be detected on some fruit near the stem end. This russet color is a medium brown (Fan 4, 177-C) at commercial maturity and lightens to a light brown (Fan 4, sheet 165-B) after the fruit has ripened.

*Fruit lenticels.*—Numerous, small and inconspicuous lenticels are typically present over the entire fruit surface area.

*Fruit lenticels.*—Surface shape — roughly globose in form and having a dimension of about 0.5 mm. in diameter and a grey color (Fan 4, sheet 197-B). Lenticels on more ripened fruit are more conspicuous, especially over the yellow areas of ground color, if present, on the fruit. Lenticels appearing on yellow ground color surfaces appear with areolar dots of red (Fan 1, sheet 42-C). This surrounds the respective lenticels.

*Fruit flesh.*—Color — White throughout (Fan 34, sheet 155-B).

*Flesh fibers.*—Numbers — A few can occasionally be present, and these are more cream colored (Fan 4, sheet 158-C) relative to the flesh itself.

*Flesh texture.*—After ripened fruit has a fine-texture, which is considered smooth, buttery and very juicy. Only a few stone cells are present in the flesh. Those stone cells which are located are typically found in the core, and core line areas.

*Fruit flavor.*—Considered very good for the species. The flavor is sweet and mild but with a pleasant fruitiness. The fruit of the present variety is less acidic than the fruit produced by the 'Bartlett' pear tree (unpatented).

*Fruit aroma.*—Generally speaking, the aroma is distinct and somewhat fruity and pleasant.

*Fruit storage.*—The present variety hangs well on the tree. Storage characteristics of this variety have not been fully tested for extended periods of time, but early indications are that it is at least equal in storage ability to either its parents. The fruit ripens uniformly after harvest.

*Resistance to insects and diseases.*—No particular susceptibilities were noted. The present variety has not been tested to expose or detect any susceptibilities or resistance to any known plant and/or fruit diseases other than those which are common to the 'Bartlett' pear tree varieties.

Although the new variety of pear tree possesses the described characteristics when grown under the ecological conditions prevailing near Phoenix, Oreg., it should be understood the variations of the usual magnitude and characteristics incident to changes and growing conditions, fertilization, pruning, pest control and horticulture management are to be expected. The foregoing description does not constitute a commercial warranty. Consequently, this disclosure may not be relied upon that the present variety, when grown, under conditions other than Phoenix, Oreg. will display each of the characteristics as provided for and described in the present application. Therefore, the foregoing description may not be relied upon to support claims of breach of warranty or merchantability or fitness for any particular purpose which is directed to the present variety.

Having thus described and illustrated my new variety of pear tree, what I claim is new and desire to secure by Plant Letters Patent is:

1. A new and distinct variety of pear tree substantially as illustrated and described and which is characterized principally as to novelty by producing an attractively colored red pear which is mature for harvesting and shipment beginning approximately after 18 September under the ecological conditions prevailing in Phoenix, Oreg.

* * * * *

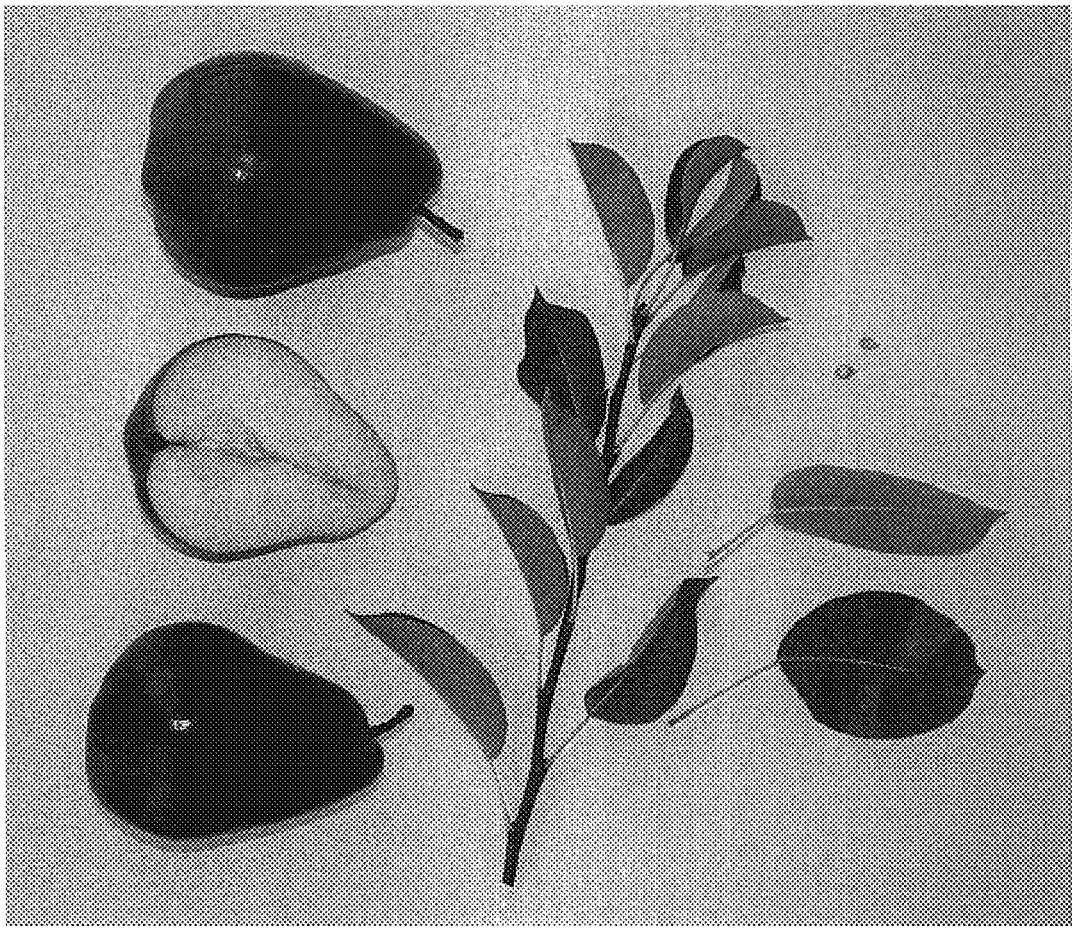

UNITED STATES PATENT AND TRADEMARK OFFICE

CERTIFICATE OF CORRECTION

PATENT NO. : PP 19,552 P3
APPLICATION NO. : 11/386183
DATED : December 9, 2008
INVENTOR(S) : David Lowry It is certified that error appears in the above-identified patent and that said Letters Patent is hereby corrected as shown below:

Title Pg, Item (57) Abstract, replace "shipment approximately" with --shipment beginning approximately--.

Column 3, after TREE, please insert --*Size.—Generally* — Medium as compared to other common pear varieties.--.

Column 7, line 6, replace "The present of the seed" with --The presence of the seed--.

Column 8, line 11, replace "when the fruit is out." with --when the fruit is cut.--.

Signed and Sealed this

Ninth Day of June, 2009

JOHN DOLL
*Acting Director of the United States Patent and Trademark Office*